United States Patent [19]

Mufti et al.

[11] 4,156,776

[45] May 29, 1979

[54] SUCROSE DERIVATIVES

[75] Inventors: Khizar S. Mufti, Reading; Riaz A. Khan, Sonning, both of England

[73] Assignee: Tate & Lyle Ltd., London, England

[21] Appl. No.: 800,312

[22] Filed: May 25, 1977

Related U.S. Application Data

[63] Continuation of Ser. No. 564,643, Apr. 3, 1975, abandoned.

[51] Int. Cl.$^2$ .............................................. C07H 9/02
[52] U.S. Cl. .......................................... 536/1; 106/25; 106/162; 536/18; 536/119; 536/120; 536/122
[58] Field of Search .................................... 536/1, 119

[56] References Cited

U.S. PATENT DOCUMENTS

| | | | |
|---|---|---|---|
| 3,198,784 | 8/1965 | Griscom et al. | 536/119 |
| 3,231,562 | 1/1966 | Mori et al. | 536/119 |
| 3,751,409 | 8/1973 | Lee | 536/119 |

*Primary Examiner*—Johnnie R. Brown
*Attorney, Agent, or Firm*—Ostrolenk, Faber, Gerb & Soffen

[57] ABSTRACT

A novel cyclic acetal derivative of sucrose, 4,6-O-isopropylidenesucrose, is prepared by treating sucrose with 2,2-dimethoxypropane in N,N-dimethylformamide, in the presence of p-toluenesulphonic acid, suitably at room temperature. The product is conveniently isolated in the form of its hexa-acetate or hexabenzoate, by treatment with acetic anhydride or benzoyl chloride, respectively, in pyridine. The resulting compounds are valuable as synthetic intermediates and in conformational investigations.

6 Claims, No Drawings

SUCROSE DERIVATIVES

This is a Continuation of application Ser. No. 564,643, filed Apr. 3, 1975, now abandoned.

This invention relates to sucrose derivatives. More particularly, the invention provides a new cyclic acetal derivative of sucrose which is useful as an intermediate in the synthesis of other sucrose derivatives.

Cyclic acetal derivatives of sugars are valuable as synthetic intermediates and in conformational investigations, but such derivatives of sucrose have in the past defied preparation, mainly due to the ready hydrolysis of the glycosidic bond. Recently, the 4,6-O-benzylidene derivative of sucrose has been prepared by the treatment of sucrose with benzylidene bromide in pyridine; but this method gives a low yield of product (generally under 35%) and the reagents involved are expensive, so there is still a need for a readily prepared cyclic acetal derivative of sucrose.

It has now been discovered that 4,6-O-isopropylidenesucrose, can be prepared by treating sucrose with 2,2-dimethoxypropane in N,N-dimethylformamide, in the presence of p-toluenesulphonic acid. This reaction is suitably performed at room temperature, and is capable of giving yields of over 50%.

The 4,6-O-isopropylidenesucrose is conveniently isolated from the reaction mixture as its hexa-acetate having the formula:

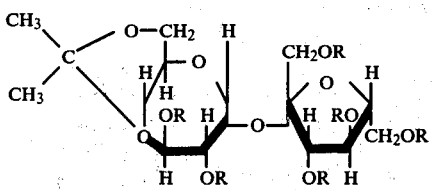

(wherein R represents an acetyl group). In order to prepare the hexa-acetate, the reaction mixture is first neutralized, suitably by using an anion exchange resin such as "Amberlite IR45" in the hydroxyl form. After filtering off the resin, the neutralized solution is concentrated to a syrup which is then treated with acetic anhydride in pyridine. The resulting hexa-acetate can be recovered and purified by conventional means, for example by diluting the reaction mixture with dichloromethane, washing successively with aqueous sodium bicarbonate and water, drying over anhydrous sodium sulphate, filtering, concentrating the filtrate to a syrup, and chromatographing this syrup on a column of silica gel, using a mixture of ether and light petroleum.

The 4,6-O-isopropylidenesucrose hexa-acetate can be hydrolyzed, for example by treatment with aqueous acetic acid, to give the know 1',2,3,3',4',6'-hexa-O-acetylsucrose having the formula:

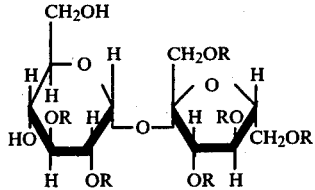

(wherein R represents an acetyl group).

The 4,6-O-isopropylidenesucrose can also be isolated from the reaction mixture in the form of other esters. For example, 4,6-O-isopropylidenesucrose hexabenzoate, having the above formula (I) wherein R represents a benzoyl group, can be prepared by neutralizing the reaction mixture with an anion exchange resin, as described hereinbefore, concentrating the neutralised solution to a syrup, and treating this syrup with benzoyl chloride in pyridine. The resulting hexabenzoate can be recovered and purified by conventional means, for example by pouring the reaction mixture into ice-water, recovering the precipitate which forms and washing it with water, taking up the residue in methylene chloride, washing the resulting solution with aqueous sodium bicarbonate and water, drying over anhydrous sodium sulphate, concentrating the solution, and crystallizing from ethanol. The 4,6-O-isopropylidenesucrose hexabenzoate can be hydrolyzed, for example by treatment with aqueous acetic acid, to give 1',2,3,3',4',6'-hexa-O-benzoylsucrose, having the above formula (II) wherein R represents a benzoyl group.

The hexa-acetylsucrose and hexa-benzoylsucrose erivatives of formula (II) are useful as a component of inks, adhesives, coatings and plastic objects as shown by Griscom U.S. Pat. No. 3,198,784, and also as intermediates in the synthesis of various 4-or 6-mono-functional and 4,6-difunctional derivatives of sucrose, for example sulphonates, azides, halo-, deoxy- and keto- drivatives, thiocyanates, disulphides, thioacetates, amines, acryloyl esters and vinyl ethers.

As an alternative to recovering it from the reaction mixture in the form of one of its esters, the 4,6-O-isopropylidenesucrose itself can be isolated by subjecting the reaction mixture to chromatography, for instance on a column of silica gel eluted with a mixture of methylene chloride and acetone. The 4,6-O-isopropylidenesucrose can also be obtained by the catalytic de-esterification of the hexa-acetate or hexabenzoate, for instance with sodium methoxide.

The invention is illustrated by the following Examples.

EXAMPLE 1

4,6-O-isopropylidenesucrose hexa-acetate

A solution of 5 g of sucrose in 200 ml of N,N-dimethylformamide was stirred with 20 ml of 2,2-dimethoxypropane and 150 mg of p-toluenesulphonic acid at room temperature for 1¼ hours. The reaction mixture was then neutralized by stirring for 15 minutes with about 10 g of "Amberlite IR45" (Trade Mark) anion exchange resin in the hydroxyl form. The mixture was filtered, and the colourless filtrate was evaporated under reduced pressure at 60°–70° C. The resulting syrup was dissolved in 150 ml of pyridine, and this solution was treated with 20 ml of acetic anhydride at room temperature for 16 hours. The solution was then concentrated by codistillation with toluene and chromatographed on a column of 150 g of silica gel (Merck "Silica gel 60". 70–230 mesh ASTAM) eluted with a 2:1 by volume mixture of ether and light petroleum. The eluate was concentrated, giving 5.9 g of the desired product. Yield: 55% $[\alpha]_D^{25} = +46°$ (c=0.2, chloroform).

Analysis: Calculated for $C_{27}H_{38}O_{17}$: C, 52.1%, H, 6.0%. Found: C, 52.1%, H, 6.0%.

NMR (100 MHz, $CDCl_3$):τ:4.36(d, 1 proton, $J_{1,2}$4.0 Hz, H-1);

5.18(q, 1 proton, $J_{2,3}$10.0 Hz, H-2);

4.64 (t, 1 proton, $J_{3,4}$10.0 Hz, H-3);

4.6 (d, 1 proton, $J_{3',4'}$6.0 Hz, H-3');

4.62 (t, 1 proton, J$_{4',5'}$6.0 Hz, H-4');
7.68–7.98 (m, 18 protons 6 Ac);
8.46–8.86 (6 protons, 2 CH$_3$).

EXAMPLE 2

1',2,3,3',4',6'-Hexa-O-acetylsucrose

A solution of 2 g of 4,6-O-isopropylidenesucrose hexa-acetate in 20 ml of glacial acetic acid was treated with 20 ml of water at 80° C. for 10 minutes. Thin layer chromatography in ether showed a slow-moving product which was coincident with a standard sample of the desired compound. The reaction solution was concentrated by codistillation with toluene, giving 1.7 g of the desired product. Yield:91.8%.

The IR, NMR and mass spectra of the product were identical with those of a standard sample.

EXAMPLE 3

4,6-O-Isopropylidenesucrose hexabenzoate

A solution of 10 g of sucrose in 200 ml of N,N-dimethylformamide was stirred with 40 ml of 2,2-dimethoxypropane and 300 mg of p-toluenesulphonic acid at room temperature for 1¼ hours. The reaction mixture was then neutralized by stirring for 15 minutes with about 10 g of "Amberlite IR45" (Trade Mark) anion exchange resin in the hydroxyl form. The resin was filtered off and the colourless filtrate was evaporated under reduced pressure at 60°–70° C. The resultant syrup was dissolved in 300 ml of pyridine and then treated with 40 ml of benzoyl chloride at 0° C. The reaction mixture was then stored at room temperature for 24 hours, after which it was poured into ice-water mixture. The precipitate which formed was filtered off and washed well with water. The residue was taken up in methylene chloride, and the resulting solution was washed with aqueous sodium bicarbonate solution and water. The organic layer was dried over anhydrous sodium sulphate, concentrated and crystallized from ethanol at room temperature to give 8.8 g of 4,6-O-isopropylidenesucrose hexabenzoate. Yield: 30%. Melting point: 168°–170° C. $[\alpha]_D^{20}=+45.7°$ (c=1.06, chloroform).

Analysis: Calculated for C$_{57}$H$_{50}$O$_{17}$: C, 68.0%, H, 4.98% Found: C,67.8%, H, 4.90%

NMR (100 MHz, CDCl$_3$):τ:
:4.04(d, 1 proton, J$_{1,2}$3.5 Hz, H-1);

4.74(q, 1 proton, J$_{2,3}$10.0Hz, H-2);
4.13(t, 1 proton, J$_{3,4}$10.0Hz, H-2);
4.03(d, 1 proton, J$_{3',4'}$5.0Hz, H-3');
4.02(t, 1 proton, J$_{4',5'}$5.0 Hz, H-4');
1.78–2.94(m, 30 protons, 6 Bz);
8.55 and 8.67(s, 6 protons, 2 CH$_3$).

The identical product was obtained on benzoylation of 4,6-O-isopropylidenesucrose, using benzoyl chloride in pyridine.

EXAMPLE 4

1',2,3,3',4',6'-Hexa-O-benzoylsucrose

A solution of 3 g of 4,6-O-isopropylidenesucrose hexabenzoate in 100 ml of glacial acetic acid, 15 ml of acetone and 28 ml of water was heated at 90° C. for 1½ hours. Thin layer chromatography of the resulting solution in ether showed a slow-moving product. The reaction solution was concentrated by codistillation with toluene to a syrup which crystallized from a mixture of ether and light petroleum, to give 2.6 g of 1',2,3,3',4',6'-hexa-O-benzoylsucrose. Yield: 90%. Melting point: 124°–125° C. $[\alpha]_D^{20}=+58.6°$ (c=1.03, chloroform)

Analysis: Calculated for C$_{54}$H$_{46}$O$_{17}$: C, 67.1%, H, 4.76%. Found: C, 67.1%, H, 4.7%.

NMR (100MHz, CDCl$_3$):τ: 4.03(d, 1 proton, J$_{1,2}$3.5 Hz, H-1);
4.72(q, 1 proton, J$_{2,3}$10.0 Hz, H-2);
4.0(d, 1 proton, J$_{3',4'}$6.5 Hz, H-3');
4.07(t, 1 proton, J$_{4',5'}$6.5 Hz, H-4');
6.81 and 7.5 7.5(2 protons, 2OH);
1.85–3.0(m, 30 protons, 6 Bz).

We claim:
1. 4,6-O-Isopropylidenesucrose.
2. 4,6-O-Isopropylidenesucrose hexa-acetate.
3. 4,6-O-Isopropylidenesucrose hexabenzoate.
4. A process for preparing 4,6-O-isopropylidenesucrose, which comprises treating sucrose with 2,2-dimethoxypropane in N,N-dimethylformamide in the presence of p-toluenesulphonic acid.
5. The process of claim 4 wherein the 4,6-O-isopropylidenesucrose is isolated from the reaction mixture by esterifying said product, isolating the resulting ester and then de-esterifying the ester to regenerate the desired product.
6. The process of claim 5, wherein said product is esterified with benzoyl chloride so as to form 4,6-O-isopropylidenesucrose hexabenzoate.

* * * * *